United States Patent

Föry

Patent Number: 5,403,814
Date of Patent: Apr. 4, 1995

[54] SULFONYLUREAS
[75] Inventor: Werner Föry, Riehen, Switzerland
[73] Assignee: Ciba-Geigy Corporation, Ardsley, N.Y.
[21] Appl. No.: 224,393
[22] Filed: Apr. 7, 1994

Related U.S. Application Data

[63] Continuation of Ser. No. 94,824, Jul. 20, 1993, abandoned, which is a continuation-in-part of Ser. No. 938,036, Nov. 12, 1992, abandoned.

[30] Foreign Application Priority Data

Mar. 25, 1991 [CH] Switzerland .................. 895/91

[51] Int. Cl.$^6$ ................... C07D 401/12; A01N 43/54
[52] U.S. Cl. .................... 504/215; 544/320; 544/321; 544/324; 544/331
[58] Field of Search ............... 504/215; 544/320, 321, 544/324, 331

[56] References Cited

U.S. PATENT DOCUMENTS

| | | | |
|---|---|---|---|
| 4,522,645 | 6/1985 | Levitt | 71/93 |
| 4,544,401 | 10/1985 | Levitt | 71/92 |
| 4,579,583 | 4/1986 | Fory | 71/92 |
| 4,690,707 | 9/1987 | Fory | 71/93 |
| 4,798,837 | 1/1989 | Drabek et al. | 514/594 |
| 4,980,506 | 12/1990 | Drabek et al. | 564/442 |
| 5,107,017 | 4/1992 | Drabek et al. | 560/358 |
| 5,153,224 | 10/1992 | Drabek et al. | 574/594 |

FOREIGN PATENT DOCUMENTS

| | | |
|---|---|---|
| 616239 | 8/1989 | Australia . |
| 634239 | 12/1990 | Australia . |
| 0103543 | 3/1984 | European Pat. Off. . |
| 179022 | 4/1986 | European Pat. Off. . |
| 0327251 | 8/1989 | European Pat. Off. . |
| 327504 | 8/1989 | European Pat. Off. . |
| 402316 | 12/1990 | European Pat. Off. . |

OTHER PUBLICATIONS

Organic Reactions vol. 29, pp. 136–139 & 161 (1983).
B. Castro, et al. Bull. Soc. Chim. FR. Part 2, (1974) pp. 3004–3014.
J. Gupton et al. Synthetic Communications, 12(9), 695–700 (1982).
Advances in Org. Chem. E. H. Böhme & H. G. Viehe, Ed. Method and Results, vol. 9(1) pp. 421–532, J. Wiley & Sons, N.Y. (1976).

Primary Examiner—John M. Ford
Attorney, Agent, or Firm—Marla J. Mathias; George Dohmann

[57] ABSTRACT

N-pyridinesulfonyl-N'-pyrimidinyl- and -triazinyl-ureas of formula I

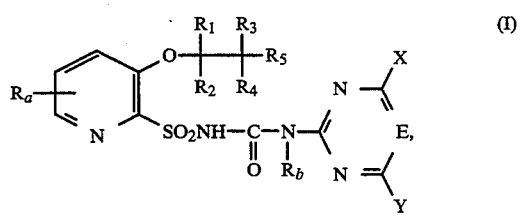

wherein
$R_1$ is hydrogen or fluorine;
or $R_1$ together with $R_3$ is a $C_2$–$C_4$alkylene chain;
$R_3$ is hydrogen, fluorine or $C_1$–$C_3$alkyl;
$R_2$ is hydrogen, fluorine or $C_1$–$C_3$alkyl;
$R_4$ is hydrogen, fluorine, chlorine or $C_1$–$C_3$alkyl;
$R_5$ is hydrogen, fluorine, chlorine, $C_1$–$C_3$alkyl, or $C_1$–$C_3$alkyl substituted by fluorine or chlorine;
$R_a$ is hydrogen or halogen, or a $C_1$–$C_4$alkyl, $C_1$–$C_4$alkoxy or $C_1$–$C_4$alkylthio radical each of which may be unsubstituted or mono- or poly-substituted by halogen;
$R_b$ is hydrogen or a $C_1$–$C_4$alkyl radical;
X is $C_1$–$C_3$alkyl, $C_1$–$C_3$alkyl mono- to tri-substituted by halogen, $C_1$–$C_3$alkoxy, or $C_1$–$C_3$alkoxy mono- to tri-substituted by halogen;
Y is halogen, $C_1$–$C_3$alkyl, $C_1$–$C_3$alkyl mono- to tri-substituted by halogen, $C_1$–$C_3$alkoxy, or
$C_1$–$C_3$alkoxy mono- to tri-substituted by halogen, or is cyclopropyl, methylamino or dimethylamino; and
E is nitrogen or the methine group, and the salts of those compounds, with the proviso that at least one of the radicals $R_1$ to $R_5$ is fluorine, or one of the radicals $R_4$ and $R_5$ is chlorine, have good selective-herbicidal properties. The preparation of those compounds and their use as herbicidal active ingredients is described.

15 Claims, No Drawings

SULFONYLUREAS

This is a continuation of Ser. No. 094,824, filed Jul. 20, 1993, now abandoned, which in turn is a continuation-in-part of Ser. No. 938,036, filed Nov. 12, 1992, now abandoned.

The present invention relates to novel herbicidally active and plant-growth-regulating N-pyridinesulfonyl-N'-pyrimidinyl- and -triazinyl-ureas, to processes for the preparation thereof, to compositions comprising them as active ingredients, and to the use thereof for controlling weeds, especially selectively in crops of useful plants, or for regulating and inhibiting plant growth.

Urea compounds, triazine compounds and pyrimidine compounds having herbicidal action are generally known. For example European Patent No. 103 543 and U.S. Pat. No. 4,544,401 describe herbicidally active and plant-growth-regulating N-pyridinesulfonyl-N'-pyrimidinyl- and -triazinyl-ureas. The compounds disclosed therein are not, however, always able to satisfy requirements in respect of potency and selectivity. There is accordingly a need for compounds that have improved activity and are more selective.

Novel sulfonylureas having improved herbicidal and plant-growth-regulating properties have now been found.

The N-pyridinesulfonyl-N'-pyrimidinyl- and -triazinyl-ureas according to the invention correspond to formula I

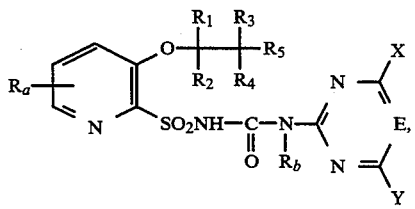

wherein
$R_1$ is hydrogen or fluorine;
or $R_1$ together with $R_3$ is a $C_2$–$C_4$alkylene chain;
$R_3$ is hydrogen, fluorine or $C_1$–$C_3$alkyl;
$R_2$ is hydrogen, fluorine or $C_1$–$C_3$alkyl;
$R_4$ is hydrogen, fluorine, chlorine $C_1$–$C_3$alkyl;
$R_5$ is hydrogen, fluorine, chlorine, $C_1$–$C_3$alkyl, or $C_1$–$C_3$alkyl substituted by fluorine or chlorine;
$R_a$ is hydrogen or halogen, or a $C_1$–$C_4$alkyl, $C_1$–$C_4$alkoxy or $C_1$–$C_4$alkylthio radical each of which may be unsubstituted or mono- or poly-substituted by halogen;
$R_b$ is hydrogen or a $C_1$–$C_4$alkyl radical;
X is $C_1$–$C_3$alkyl, $C_1$–$C_3$alkyl mono- to tri-substituted by halogen, $C_1$–$C_3$alkoxy, or $C_1$–$C_3$alkoxy mono- to tri-substituted by halogen;
Y is halogen, $C_1$–$C_3$alkyl, $C_1$–$C_3$alkyl mono- to tri-substituted by halogen, $C_1$–$C_3$alkoxy, or $C_1$–$C_3$alkoxy mono- to tri-substituted by halogen, or is cyclopropyl, methylamino or dimethylamino; and
E is nitrogen or the methine group,
and the salts of those compounds, with the proviso that at least one of the radicals $R_1$ to $R_5$ is fluorine, or one of the radicals $R_4$ and $R_5$ is chlorine.

Suitable substituents $R_2$ to $R_5$ representing alkyl groups are straight-chain or branched alkyl groups, for example methyl, ethyl, n-propyl and isopropyl.

The alkyl groups occurring as or in the substituent $R_a$ include straight-chain or branched alkyl groups, such as, for example, methyl, ethyl, n-propyl, isopropyl, n-butyl, sec-butyl, isobutyl or tert-butyl. Those alkyl groups may be mono- or poly-substituted by halogen, halogen being in particular fluorine, chlorine, bromine or iodine. Of these alkyl groups mono- or poly-substituted by halogen preference is given to those alkyl groups that are mono- to tri-substituted by halogen, especially fluorine or chlorine. Especially preferred alkyl groups mono- to tri-substituted by fluorine or chlorine are e.g. trifluoromethyl, 1-fluoroethyl, 1,1-dichloroethyl, 3,3,3-trifluoropropyl, 2-fluoroisopropyl and 3-fluoropropyl.

Alkyl groups mono- or poly-substituted by fluorine or chlorine present as the substituent $R_5$ include straight-chain or branched alkyl groups mono- to tri-substituted by fluorine or chlorine, e.g. dichloromethyl or trifluoromethyl.

The $C_1$–$C_3$alkyl radicals present as or in the substituents X and Y include in particular methyl, ethyl, n-propyl and isopropyl, especially methyl or ethyl, and also the haloalkyls derived from those radicals that are mono- to tri-substituted by halogen. Of the $C_1$–$C_3$alkyl groups mono- to tri-substituted by halogen present in the substituents X and Y, $C_1$–$C_3$alkyl groups that are mono- to tri-substituted by fluorine or chlorine are preferred. Especially preferred $C_1$–$C_3$alkyl groups mono- to tri-substituted by halogen present in the substituents X and Y are, for example, trifluoromethyl, difluoromethyl, 2-chloroethyl, chlorodifluoromethyl, dichloromethyl, chlorofluoromethyl, 1,1-dichloroethyl, 2,2,2-trifluoroethyl, 3,3,3-trifluoropropyl or 2,3-dichloropropyl, with fluoromethyl, chloromethyl, difluoromethyl and trifluoromethyl being most especially preferred.

Alkylthio is, for example, methylthio, ethylthio, propylthio, isopropylthio, n-butylthio, isobutylthio, sec-butylthio or tert-butylthio.

Alkoxy is, for example, methoxy, ethoxy, propoxy, iso-propoxy, n-butoxy, iso-butoxy, sec-butoxy or tert-butoxy; preferably methoxy or ethoxy.

There come into consideration as a $C_2$–$C_4$alkylene chain denoted by $R_1$ and $R_3$ ethylene, propylene or butylene.

The invention also includes the salts that the compounds of formula I can form with amines, alkali metal and alkaline earth metal bases or quaternary ammonium bases.

Of the alkali metal and alkaline earth metal hydroxides as salt-formers, prominence is to be given to the hydroxides of lithium, sodium, potassium, magnesium and calcium, but especially to the hydroxides of sodium and potassium.

Examples of amines that are suitable for salt formation are primary, secondary and tertiary aliphatic and aromatic amines, such as methylamine, ethylamine, propylamine, isopropylamine, the four isomers of butylamine, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, but especially ethyl-, propyl-, diethyl- or triethyl-amine, and more especially isopropylamine and diethanolamine.

Examples of quaternary ammonium bases are generally the cations of haloammonium salts, for example the tetramethylammonium cation, the trimethylbenzylammonium cation, the triethylbenzylammonium cation, the tetraethylammonium cation and the trimethylethylammonium cation, but also the ammonium cation.

Preferred are compounds of formula I wherein $R_1$ and $R_3$, each independently of the other, are hydrogen or fluorine; $R_2$ is hydrogen, fluorine or $C_1$–$C_3$alkyl; $R_4$ is hydrogen, fluorine or chlorine; and $R_5$ is hydrogen or fluorine, or $C_1$–$C_3$alkyl that is unsubstituted or substituted by fluorine or chlorine, and $R_a$, $R_b$, X, Y and E are as defined for formula I, and the compounds N-[3-(2,5-dichloro-2-methylpropoxy)-pyrid-2-yl-sulfonyl]-N'-(4,6-bis-difluoromethoxy-pyrimidin-2-yl)urea and N-[3-(2,5-dichloro-2-methylpropoxy)-pyrid-2-yl-sulfonyl]-N'-(4,6-bis-difluoromethoxy- 1,3,5-triazin-2-yl)urea.

Of the compounds of formula I and also of the preferred compounds of formula I those wherein $R_a$ and $R_b$ are each hydrogen are especially preferred.

Also especially preferred are compounds of formula I, including all of the above-mentioned preferred compounds, wherein the radical of formula Ia

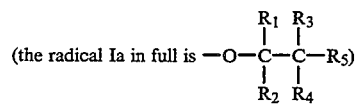

(the radical Ia in full is $-O-\overset{R_1}{\underset{R_2}{C}}-\overset{R_3}{\underset{R_4}{C}}-R_5$)

contains a maximum of 3 carbon atoms.

Most especially preferred are compounds of formula I, including all of the above-mentioned preferred compounds, wherein at least one of the radicals $R_3$, $R_4$ and $R_5$ in the radical of formula Ia is a halogen atom, i.e. $R_3$ is a fluorine atom, and each of $R_4$ and $R_5$, independently of the other, is a fluorine or a chlorine atom. In those compounds, the oxygen atom is separated from the halogen atom in the radical $R_3$, $R_4$ or $R_5$ by 2 carbon atoms. Especially preferred among such compounds of formula Ia are those wherein only one of the radicals $R_3$, $R_4$ and $R_5$ is a halogen atom, i.e. $R_3$ is fluorine, $R_4$ is fluorine or chlorine, or $R_5$ is fluorine or chlorine. In those most especially preferred compounds of formula I, preferably $R_1$ is hydrogen and $R_2$ is hydrogen or $C_1$–$C_3$alkyl.

Important compounds of formula I, including all the above-mentioned preferred compounds, are those wherein one of the radicals X and Y is methyl, methoxy, ethoxy, difluoromethoxy or chlorine.

Most especially important are compounds of formula I, including all of the mentioned preferred compounds, wherein E is the methine bridge.

In the compounds of formula I, the radicals preferably have the following meanings:

$R_1$ is hydrogen or fluorine;
$R_2$ is hydrogen, fluorine, methyl or ethyl;
$R_3$ is hydrogen, fluorine or methyl, or $R_3$ together with $R_1$ is a $C_4$alkylene chain;
$R_4$ is hydrogen, fluorine, chlorine, methyl or ethyl;
$R_5$ is hydrogen, fluorine, chlorine, trifluoromethyl or dichloromethyl;
$R_a$ and $R_b$ are each hydrogen;

X is methyl, methoxy, ethoxy, difluoromethoxy or 2,2,2-trifluoroethoxy;
Y is chlorine, methyl, cyclopropyl, methoxy, difluoromethoxy, methylamino or dimethylamino; and
E is nitrogen or the methine group.

The following compound may be mentioned as a preferred individual compound from the scope of formula I:

N-[3-(2-chloroethoxy)-pyridine-2-sulfonyl]-N'-(4,6-dimethoxypyrimidin-2-yl)urea.

The compounds of formula I are prepared by reacting a 3-haloalkoxy-pyrid-2-yl-sulfonamide of formula II

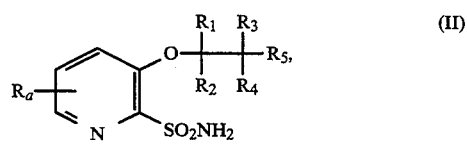

wherein $R_a$, $R_1$, $R_2$, $R_3$, $R_4$ and $R_5$ are as defined for formula I, with a pyrimidinyl or triazinyl carbamate of formula III

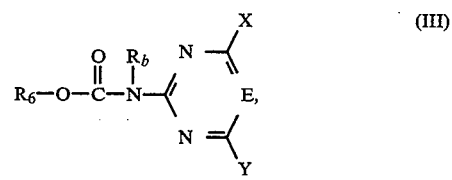

wherein X, Y, $R_b$ and E are as defined for formula I and $R_6$ is phenyl that may be substituted by $C_1$–$C_4$alkyl or by halogen, in an inert organic solvent in the presence of a base.

According to another process for the preparation of the compound of formula I a 3-alkoxy-pyridylsulfonamide of formula II in an inert solvent or diluent is reacted with an isocyanate of formula IV

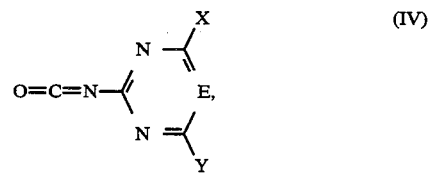

wherein X, Y and E are as defined for formula I.

The N-pyridinesulfonyl-N'-pyrimidinyl- and -triazinyl-sulfonylureas of formula I are also prepared by reacting a pyridylsulfonamide of formula V

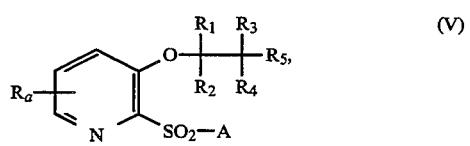

wherein $R_a$, $R_1$, $R_2$, $R_3$, $R_4$ and $R_5$ are as defined for formula I and A is a radical

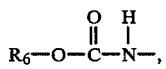

wherein $R_6$ has the meaning given, or a radical O=C=N—, in the presence of a base with a 2-amino-pyrimidine or -triazine of formula Va

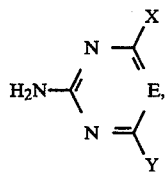

wherein E, X and Y are as defined for formula I.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide or diethylformamide, or N-methylpyrrolidone. The reaction temperatures are preferably from $-20°$ to $+120°$ C.

The reactions are generally slightly exothermic and can be carried out at room temperature. In order to reduce the reaction time or also to initiate the reaction, it is expedient to heat the reaction mixture to boiling point briefly. The reaction times can also be reduced by adding a few drops of base as a reaction catalyst. Suitable bases are especially tertiary amines, such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. Other bases that may be used, however, are inorganic bases, such as hydrides, e.g. sodium or calcium hydride, hydroxides, e.g. sodium and potassium hydroxide, carbonates, e.g. sodium and potassium carbonate, or hydrogen carbonates, e.g. potassium and sodium hydrogen carbonate.

The end products of formula I can be isolated by concentration and/or evaporation of the solvent and can be purified by recrystallisation or trituration of the solid residue in solvents in which they are not readily soluble, such as ethers, aromatic hydrocarbons or chlorinated hydrocarbons.

The intermediates of formulae IV and V are known or can be prepared analogously to known processes. Processes for the preparation of N-pyrimidinyl and N-triazinyl carbamates are described, for example, in EP-A-101 670.

N-Pyrimidinyl and N-triazinyl isocyanates can be prepared from the corresponding 2-amino-pyrimidines and -triazines, respectively, of formula Va

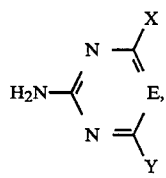

wherein X, Y and E are as defined for formula I. Such reactions and the preparation of compounds of formula III are described in EP-A-044 808. Compounds of formula Va are known from EP-A-070 804. The intermediates of formula II are novel and were developed specifically for the synthesis of the compounds of formula I. The present invention therefore also relates to them.

The same preferences with respect to $R_a$, $R_1$, $R_2$, $R_3$, $R_4$ and $R_5$ as for compounds of formula I apply to the above intermediates.

The novel intermediates of formula II can be prepared by various processes that are known per se. For example the compounds of formula II may be obtained by reacting a 3-fluoropyrid-2-yl-sulfonamide of formula VI

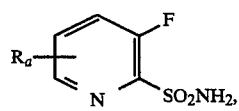

wherein $R_a$ is as defined for formula I, with an alkanol of formula VII

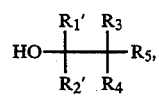

wherein $R_1'$ is hydrogen and $R_2'$ is hydrogen or $C_1$-$C_3$alkyl, or $R_1'$ together with $R_3$ is $C_2$-$C_4$alkylene, $R_3$ is as defined for formula I and $R_4$ and $R_5$ are as defined for formula I but may not be chlorine. Such reactions are described in Synth. Commun. 12(9), 695 (1982) or in EP-A-103 543.

The compounds of formula II can also be prepared by reacting a 3-fluoro-pyrid-2-ylsulfonamide of formula VI with an alkanol of formula VIIa

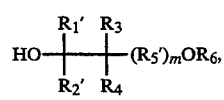

wherein $R_1'$, $R_2'$, $R_3$ and $R_4$ are as defined for formula VII, $R_5'$ is $C_1$-$C_3$alkylene, $R_6$ is benzyl or tert-butyl, and m is the integer 0 or 1, and then removing the protecting group $R_6$ again, e.g. by hydrolysis in acidic or alkaline medium or by hydrogenation, in accordance with the following synthesis scheme:

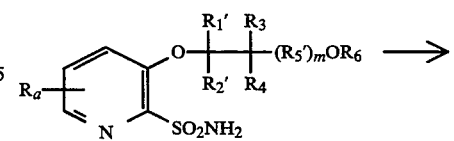

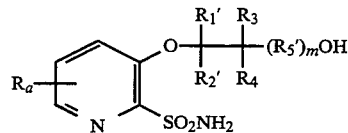

The removal of the tert-butyl protecting group in acidic medium is carried out in accordance with J. Chem. Soc. 1963, 755. A benzyl protecting group is removed e.g. with hydrogen in the presence of a catalyst; see in this connection J. Am. Chem. Soc. 93, 1746 (1971). The hydroxy group is then replaced by a chlorine atom according to a method described in EP-A-179 022, EP-A-327 504 or also in Adv. Org. Chem. 9 (Part 1), 421. The hydroxy group can also be replaced by a fluorine atom, according to a process described in Organic Reactions 1983, 513.

The intermediates of formula II may also be prepared, for example, according to the following reaction scheme:

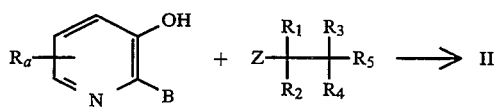

In these formulae, $R_a$, $R_1$, $R_2$, $R_3$, $R_4$ and $R_5$ are as defined for formula I, whilst Z is a suitable leaving group, for example bromine or a tolylsulfonyloxy or methylsulfonyloxy group, and B is either already the sulfonamido group or is an isopropylmercapto or benzylthio group still to be converted into the sulfonamido group, in which case it is converted into the chlorosulfonyl radical which is then convened into the sulfonamido group; see in that connection EP-A-103 543 or U.S. Pat. No. 4,522,645.

A close reaction variant for the preparation of compounds of formula IIa wherein $R_4$ is hydrogen and $R_5$ is fluorine or chlorine is shown by the following reaction scheme:

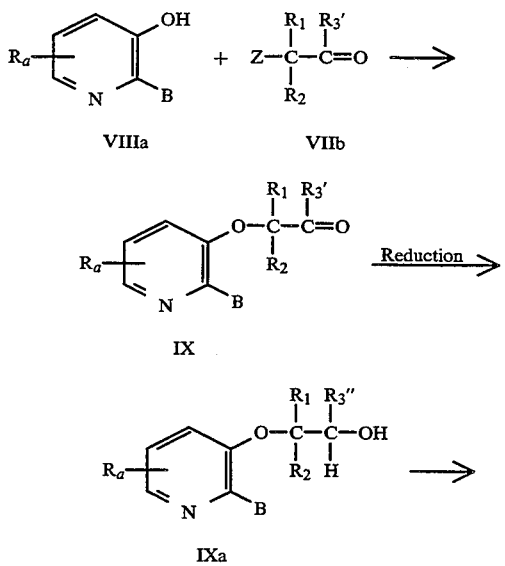

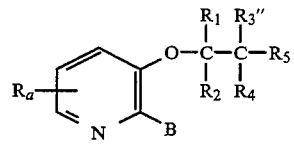

wherein $R_a$, B, Z, $R_1$ and $R_2$ have the meanings given, $R_3'$ is hydrogen, $C_1$–$C_3$alkyl or $C_1$–$C_3$alkoxy, $R_3''$ is hydrogen or $C_1$–$C_3$alkyl, and $R_1$ together with $R_3'$, and $R_1$ together with $R_3''$, is also a $C_2$–$C_4$alkylene chain. The reaction of the compounds of formula IXa to form the compounds of formula IIa is carried out according to a method described in EP-A-179 022, EP-A-327 504 or also in Adv. Org. Chem. 9 (Part 1), 421. The hydroxy group may also be replaced by a fluorine atom according to a process described in Organic Reactions 1983, 513.

Furthermore, the intermediates of formula II can also be prepared by reactions in accordance with the following scheme:

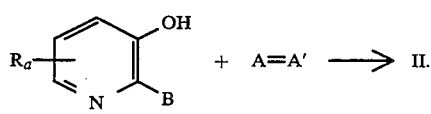

In these formulae $R_a$ is as defined for formula I, B is the sulfonamido group or an isopropylmercapto or benzylthio group that is to be converted into the sulfonamido group, whilst A=A' is a di- or poly-haloalkene that corresponds in the number of carbon atoms and halogen atoms to the radical of formula Ia. These reactions are carried out e.g. analogously to the following literature sources:

EP-A- 179 022;
EP-A-318 781;
EP-A-327 504;
L'actualité chimique, May 1987, 151;
J. Fluorine Chemistry 20, 759 (1982);
Ind. Eng. Chem. 39, 412 (1947);
J. Am. Chem. Soc. 82, 5116 (1960).

The starting compounds required for the preparation processes are either known or can easily be prepared from known compounds.

The compounds of formula VI

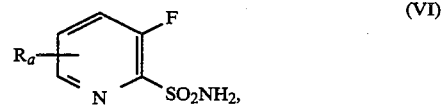

and their preparation are described in EP-A-402 316.

Starting materials of formula VIII

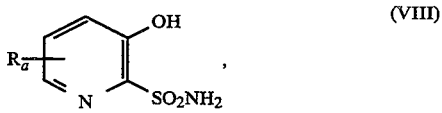

are prepared from compounds of formula VI by replacing the fluorine atom by the radical of a reactive alkanol, for example benzyl alcohol, tert-butyl alcohol, the alkane radical assuming the role of a protecting group which is then removed again by hydrolysis or hydrogenolysis. These reactions are described e.g. in EP-A-103 543 and illustrated by the following formula scheme:

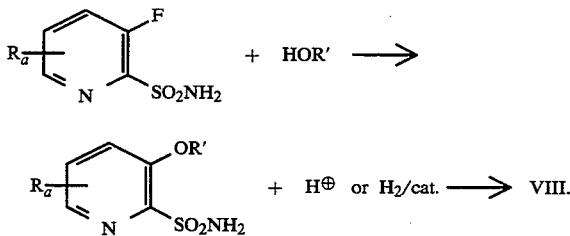

According to a method described in U.S. Pat. No. 4,522,645, the starting materials of formula VIII can also be prepared according to the scheme below:

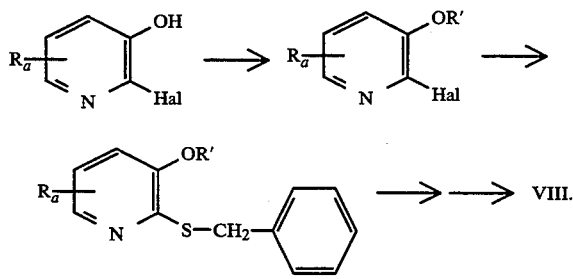

The compounds of formula I are generally used successfully at rates of application of from 0.001 to 2 kg/ha, especially from 0,005 to 1 kg/ha. The concentration required to achieve the desired effect can be determined by experiment. It is dependent on the type of action, the stage of development of the cultivated plant and of the weed, and also on the application (place, time, method) and, in dependence on those parameters, can vary within wide limits.

When used at relatively low rates of application, the compounds of formula I are distinguished by growth-inhibiting and herbicidal properties, which render them excellently suitable for use in crops of useful plants, especially in cereals, cotton, soybeans, rape, maize and flee, their use in maize crops being most especially preferred.

The invention relates also to herbicidal and plant-growth-regulating compositions comprising a novel compound of formula I, and to methods of inhibiting plant growth.

Plant growth regulators are substances that bring about agronomically desirable biochemical and/or physiological and/or morphological changes into the plant.

The active ingredients incorporated in the compositions according to the invention influence plant growth in different ways depending on the time of application, the concentration, the type of application and the environmental conditions. Plant growth regulators of formula I can, for example, inhibit the vegetative growth of plants. This type of action is valuable in the case of lawn areas, in the cultivation of ornamentals, in fruit plantations, in the case of roadside embankments and in sports fields and industrial sites, but also in the specific inhibition of side-shoots, as in the case of tobacco. In agriculture, inhibition of the vegetative growth of cereals leads, owing to a strengthening of the stalk, to reduced lodging, and similar agronomic effects are achieved in rape, sunflowers, maize and other cultivated plants. Moreover, by inhibiting the vegetative growth it is possible to increase the number of plants per unit area. Another field of use for growth inhibitors is the selective control of cover plants in plantations or widely spaced crops which is achieved by greatly inhibiting the growth of the cover crops without killing them, so that competition with the main crop is eliminated but the agronomically positive effects, such as erosion prevention, fixing of nitrogen and loose soil structure, are preserved.

A method of inhibiting plant growth is to be understood as being a method of controlling a plant's natural development without changing its life-cycle, as determined by genetic characteristics, in the sense of mutation. The method of regulating growth is applied at a time in the plant's development that has to be determined for each individual case. The compounds of formula I can be applied pre- or post-emergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions containing them for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of compound of formula I (in the case of a 50% formulation: up to 8.0 g of wettable powder) are used per 1 kg of seed.

b) Dressing the seeds with an emulsifiable concentrate of the active ingredient, or with an aqueous solution of the compound of formula I formulated as a wettable powder, according to method a) (wet dressing).

c) Dressing by soaking the seeds for a period of from 1 to 72 hours in a liquor containing up to 1000 ppm of compound of formula I and, if desired, subsequently drying the seeds (seed soaking).

Seed dressing or treatment of the germinated seedling are naturally the preferred methods of application because the treatment with the active ingredient is directed wholly at the target crop. From 0.001 g to 4.0 g of active ingredient are normally used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granulated carriers or polymerised granules (urea/-formaldehyde) and allowed to dry. If required, a coating may be applied (coated granules), which allows the active ingredient to be released in metered amounts over a specific period of time.

The compounds of formula I are used in unmodified form, as obtainable from synthesis, or, preferably, as compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouting, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, also silicone oils.

The solid carriers used, e.g. for dusts and dispersible powders, are normally natural mineral fillers such as calcite, talcum, kaolin, montmofillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutyl-naphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylendiaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyl-trimethylammonium chloride or benzyldi(2-chloroethyl)ethylammonium bromide.

The surfactants customarily employed in formulation technology are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., N.Y. 1980–1981.

Dr. Helmut Stache "Tensid-Taschenbuch", Carl Hanser Verlag, Munich/Vienna 1981.

The herbicidal and plant-growth-regulating compositions generally comprise 0.1 to 99%, preferably 0.1 to 95%, of a compound of formula I, 1 to 99% of a solid or liquid adjuvant and 0 to 25%, preferably 0.1 to 25%, of a surfactant.

Whereas commercial products will preferably be formulated as concentrates, the end user will normally employ dilute formulations.

The compositions may also comprise further additives such as stabilisers, for example vegetable oils and epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

Preferred formulations are composed in particular of the following constituents (throughout, percentages are by weight):

| Emulsifiable concentrates: | |
|---|---|
| active ingredient: | 1 to 90%, preferably 5 to 20% |
| surfactant: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

Formulation Examples for liquid active ingredients of formula I (throughout, percentages are by weight)

| 1. Emulsifiable concentrates | a) | b) | c) |
|---|---|---|---|
| a compound of Table 1 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| a compound of Table 1 | 80% | 10% | 5% | 95% |
| propylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3. Granules | a) | b) | c) | d) |
|---|---|---|---|---|
| a compound of Table 1 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is subsequently evaporated off in vacuo.

| 4. Dusts | a) | b) |
|---|---|---|
| a compound of Table 1 | 2% | 5% |
| highly dispersed silicic acid | 1% | 5% |

| 4. Dusts | a) | b) |
|---|---|---|
| talcum | 97% | — |
| kaolin | — | 90% |

Ready-for-use dusts are obtained by homogeneously mixing the carriers with the active ingredient.

Formulation Examples for solid active ingredients of formula I (throughout, percentages are by weight)

| 5. Wettable powders | a) | b) | c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
|---|---|
| a compound of Table 1 | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| a compound of Table 1 | 5% | 8% |
| talcum | 95% | — |
| kaolin | — | 92% |

Ready-for-use dusts are obtained by mixing the active ingredient with the carriers and grinding the mixture in a suitable mill.

| 8. Extruder granules | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated ganules | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrate | |
|---|---|
| a compound of Table 1 | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient is intimately mixed with the adjuvants, giving a suspension concentrate from which suspensions of any desired concentration can be obtained by dilution with water. The compounds of formula I are used in unmodified form or, preferably, as compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring, are chosen in accordance with the intended objectives and the prevailing circumstances.

PREPARATION EXAMPLES

Example P1: Preparation of 3-hydroxy-pyrid-2-ylsulfonamide (intermediate)

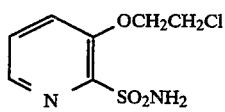

A solution of 263.7 g of 3-benzyloxy-pyrid-2-ylsulfonamide in 2.5 l of methanol is hydrogenated with the addition of 26 g of 5% Pd/C catalyst. After 23.8 l of hydrogen have been absorbed, the catalyst is filtered off. After evaporation of the methanol, 3-hydroxypyrid-2-ylsulfonamide remains in the form of a crystalline mass. Melting point 162°-164° C.

Example P2: Preparation of 3-(2-chloroethoxy)-pyrid-2-ylsulfonamide (intermediate)

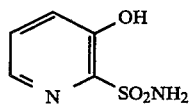

First 17.9 g of potassium carbonate and then 28.14 g of 2-(2-chloroethyl)-toluene-4-sulfonate are added, with stirring, to a solution of 17.4 g of 3-hydroxy-pyrid-2-ylsulfonamide in 240 ml of dimethylacetamide. The reaction mixture is stirred for 1.5 hours at 80° C. and then cooled and filtered. The filtration residue is washed with acetonitrile. The filtrate and the washing liquid are adjusted to pH 5–6 with trifluoroacetic acid, filtered and concentrated using a rotary evaporator. For purification the residue is chromatographed on a silica gel column using ethyl acetate/n-hexane 4/1. Removal of the eluant by evaporation yields 14.42 g of the above sulfonamide in the form of colourless crystals which melt at 136°–138° C.

Example P3: Preparation of 3-(2-fluoroethoxy)-pyrid-2,ylsulfonamide (intermediate)

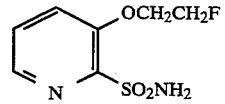

5.76 ml of 2-fluoroethanol are added dropwise, with cooling, to a suspension of 6.54 g of sodium hydride (55.6% NaH in oil) in 120 ml of tetrahydrofuran so that the temperature does not exceed 20° C. When the dropwise addition is complete, the reaction mixture is stirred at room temperature for 15 minutes and then a further solution of 10.56 g of 3-fluoro-pyrid-2-ylsulfonamide in 60 ml of tetrahydrofuran is added dropwise over a period of 10 minutes. The reaction solution is then stirred for 10 minutes at room temperature and for 2 hours at reflux before it is cooled and concentrated. For purification, the oil remaining is chromatographed on a silica gel column using ethyl acetate/hexane 4/1. Evaporation of the eluant yields a light-coloured oil which crystallises spontaneously, yielding 5.88 g of title product which melts at 122°–123° C.

Example P4: Preparation of 2-(2-isopropylthiopyrid-3-yloxy)-propionic acid methyl ester (intermediate)

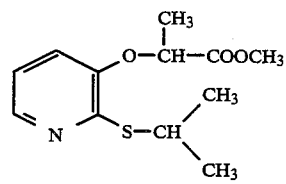

12.3 ml of 2-bromopropionic acid methyl ester are added dropwise at room temperature to a mixture of 16.9 g of 2-isopropylthio-3-hydroxypyridine and 15.2 g of potassium carbonate in 250 ml of dimethylformamide and the batch is stirred for 75 minutes. The suspension is introduced into a mixture of ice-water (300 ml), 50 ml of 2N hydrochloric acid and 300 ml of ethyl acetate, washed four times with 120 mi of water and 120 mi of ethyl acetate each time, and the organic phase is dried over sodium sulfate and concentrated by evaporation. 25.4 g of the desired intermediate are obtained in the form of a viscous oil.

Example P5: Preparation of 2-(2-isopropylthio-pyrid-3-yloxy)-propan-1-ol (intermediate)

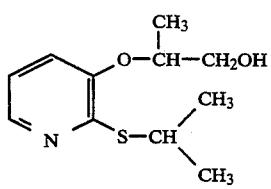

7.66 g of 2-(2-isopropylthiopyrid-3-yloxy)-propionic acid methyl ester in 40 ml of ether are added dropwise at 0°–6° C., over a period of 20 minutes, to a mixture of 0.854 g of lithium aluminium hydride in 15 ml of absolute diethyl ether, and the mixture is then stirred for one hour at 0° C. At 0° C. 0.85 ml of water, 0.85 ml of 30% sodium hydroxide solution and 2.56 ml of water are slowly added in succession to the resulting suspension, which is then stirred for one hour at room temperature to complete the reaction. The reaction solution is filtered, washed with ether and concentrated by evaporation. 6.56 g of the desired pyridyloxypropanol are obtained in the form of a colourless oil.

Example P6: Preparation of 2-isopropylthio-3-(1-fluoropropan-2-yloxy)-pyridine (intermediate)

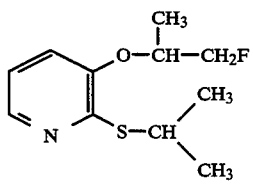

1.13 g of 2-(2-isopropylthiopyrid-3-yloxy)-propan-1-ol in 5 ml of chlorobenzene are added dropwise at −40° C., over a period of 10 minutes, to a solution of 0.89 g of diethylaminosulfur trifluoride (DAST) in 10 ml of absolute chlorobenzene. The reaction mixture is stirred for 3 hours at −30° C. and overnight at room temperature. The reaction mixture is poured onto ice-water/ethyl acetate, adjusted to pH 6–7 with saturated sodium hydrogen carbonate solution, and washed twice with water and ethyl acetate each time. The organic phase is dried over sodium sulfate and concentrated by evaporation. Purification of the reaction mixture by silica gel chromatography using ethyl acetate/n-hexane 1/8 as eluant yields 0.22 g of the desired fluorine derivative in the form of a light-yellow oil.

Example P7: Preparation of 3-(1-fluoropropan-2-yloxy)-pyrid-2-ylsulfonamide (intermediate)

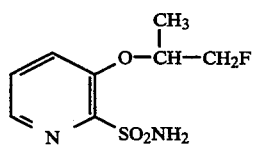

4.31 g of gaseous chlorine are introduced over a period of 10 minutes, at −5° C., into a mixture of 3.5 g of 2-isopropylthio-3-(1-fluoropropan-2-yloxy)-pyridine, 40 ml of dichloromethane and 45.6 ml of 1N hydrochloric acid. The mixture is then stirred for 15 minutes at −3° C. and, at that same temperature, nitrogen is introduced for a period of 20 minutes. The phases are washed three times with ice-water and dichloromethane each time and dried over sodium sulfate. This dichloromethane solution is then added dropwise over a period of 10 minutes, at −50° C. to −40° C., to a mixture of 3.88 g of ammonia in 15 ml of dichloromethane, and the resulting mixture is stirred for 3 hours at room temperature and subsequently filtered. The reaction solution is concentrated by evaporation, the oily residue is triturated with diethyl ether, and the crystal mass is filtered and dried. 3.2 g of the desired sulfonamide having a melting point of 104°–106° C. are obtained.

Example P8: Preparation of 2-isopropylthio-3-(cyclohexanon-2-yloxy)-pyridine (intermediate)

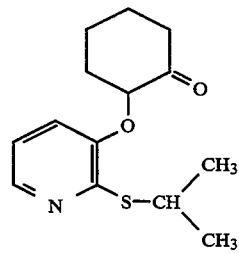

7.29 g of 2-chlorocyclohexanone are added at room temperature to a mixture of 8.4 g of 2-isopropylthio-3-hydroxypyridine and 7.6 g of potassium carbonate in 120 ml of dimethylformamide, and the mixture is stirred for one hour at 45°–50° C. After the addition of 1.46 g of 2-chlorocyclohexanone and 1.52 g of potassium carbonate and after 2 hours of a further analogous addition of 0.73 g of 2-chlorocyclohexanone and 0.76 g of potassium carbonate, the suspension is stirred for a further 3.5 hours at 45°–50° C. The resulting reaction solution is poured onto a mixture consisting of 200 ml of ice-water, 50 ml of 2N acetic acid and 100 ml of ethyl acetate, washed three times with 300 ml of ethyl acetate and 100 ml of saturated sodium chloride solution each time, dried over sodium sulfate and concentrated by evaporation. The residue is triturated with petroleum ether and filtered. 9.57 g of the desired ketone having a melting point of 106°–110° C. are obtained.

Example P9: Preparation of 2-isopropylthio-3-(1-hydroxycyclohexan-2-yloxy)-pyridine (intermediate)

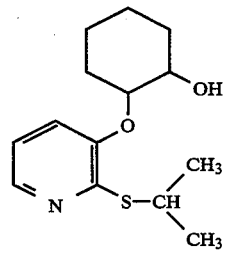

15.4 g of 2-isopropylthio-3-(cyclohexanon-2-yloxy)-pyridine in 100 ml of ether and 40 ml of dichloromethane are added dropwise at 0°–4° C., over a period of 10 minutes, to a mixture of 1.08 g of lithium aluminium hydride in 135 ml of absolute diethyl ether, and the mixture is stirred for one hour at 0°-4° C. There are slowly added dropwise in succession to that suspension, at 0° C., 1.61 ml of water, 1.61 ml of 30% sodium hydroxide solution and 4.69 ml of water, and the mixture is stirred at room temperature for one hour to complete the reaction. The reaction solution is filtered, washed with dichloromethane and concentrated by evaporation. 14.47 g of the desired pyridyloxycyclohexanol are obtained in the form of a yellow oil.

Example P10: Preparation of 2-isopropylthio-3-(1-chlorocyclohexan-2-yloxy)-pyridine (intermediate)

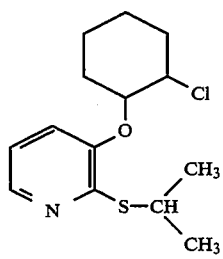

4.0 g of triphenylphosphine are added to a mixture of 3.21 g of 2-isopropylthio-3-(1-hydroxycyclohexan-2-yloxy)-pyridine and 35 ml of absolute carbon tetrachloride and the mixture is stirred for 5 hours at reflux temperature. The resulting reaction mixture is stirred into a mixture of 20 ml of dichloromethane and 20 ml of ice-water, and washed three times with dichloromethane and water each time, and the organic phase is dried over sodium sulfate and concentrated by evaporation. Purification of the wax-like residue is carried out by way of a silica gel column with ethyl acetate/n-hexane 1/19 as eluant. 0.79 g of the desired chloride is obtained in the form of a yellow oil.

Example P11: Preparation of 3-(1-chlorocyclohexan-2-yloxy)-pyrid-2-ylsulfonamide (intermediate)

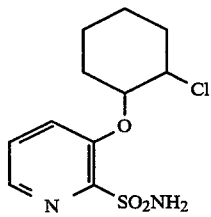

1.33 g of chlorine gas is introduced for a period of 5 minutes at −5° to 0° C. into a mixture of 1.35 g of 2-isopropylthio-3-(1-chlorocyclohexan-2-yloxy)-pyridine, 10 ml of dichloromethane and 14.1 ml of 1N hydrochloric acid. The mixture is stirred at −5° to 0° C. for 15 minutes and, at that same temperature, nitrogen is introduced for a period of 20 minutes. The phases are washed three times with ice-water and dichloromethane each time and dried over sodium sulfate. This reaction solution is then added dropwise at −50° C. to −40° C., over a period of 10 minutes, to a mixture of 2.7 g of ammonia in 10 ml of dichloromethane. The resulting reaction mixture is allowed to warm to room temperature over a period of 2 hours, filtered and the filtrate is concentrated by evaporation. 2.47 g of the desired sulfonamide having a melting point of 104°-106° C. are obtained.

Example P12: Preparation of N-[3-(2-chloroethoxy)-pyrid-2-yl-sulfonyl]-N'-(4,6-dimethoxypyrimidin-2-yl)urea

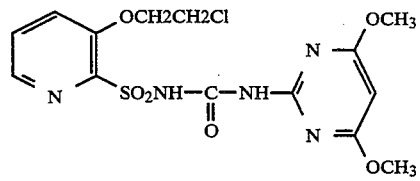

4.52 g of N-(4,6-dimethoxy-pyrimidin-2-yl)phenyl carbamate, followed by 2.46 ml of 1,5-diazabicyclo[5.4.0]undec-5-ene are added to a solution of 3.55 g of 3-(2-chloroethoxy)-pyrid-2-ylsulfonamide in 45 ml of acetonitrile. The reaction mixture is stirred at room temperature for 2 hours and then concentrated using a rotary evaporator. The oil which remains is triturated in a mixture of 10 ml of 2N hydrochloric acid and 20 ml of water. White crystals are formed, which are filtered off with suction and washed with water and ether. 4.52 g of title product, which melts at 156°-158° C., are obtained.

The compounds and intermediates listed in Tables 1 and 2 are obtained in an analogous manner to the above Examples:

TABLE 1

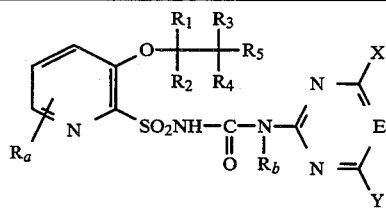

(I)

| No. | $R_a$ | $R_1$ | $R_2$ | $R_3$ | $R_4$ | $R_5$ | $R_b$ | X | Y | E |
|---|---|---|---|---|---|---|---|---|---|---|
| 1.01 | H | H | H | $CH_3$ | Cl | $CH_2Cl$ | H | $OCHF_2$ | $OCHF_2$ | CH |
| 1.02 | H | H | H | $CH_3$ | Cl | $CH_2Cl$ | H | $OCH_3$ | $CH_3$ | N |

TABLE 1-continued (I)

| No. | $R_a$ | $R_1$ | $R_2$ | $R_3$ | $R_4$ | $R_5$ | $R_b$ | X | Y | E |
|---|---|---|---|---|---|---|---|---|---|---|
| 1.03 | H | H | H | H | H | Cl | H | $OCH_3$ | $OCH_3$ | CH |
| 1.04 | H | H | H | H | H | Cl | H | $OCH_3$ | Cl | CH |
| 1.05 | H | H | H | H | H | Cl | H | $OCH_3$ | $CH_3$ | N |
| 1.06 | H | H | H | H | H | Cl | H | $OCHF_2$ | $CH_3$ | CH |
| 1.07 | H | H | H | H | H | F | H | $OCH_3$ | $CH_3$ | N |
| 1.08 | H | H | H | H | H | F | H | $OCH_3$ | Cl | CH |
| 1.09 | H | H | H | H | H | F | H | $OCH_3$ | $OCH_3$ | CH |
| 1.10 | H | H | H | H | H | F | H | $CH_3$ | $CH_3$ | CH |
| 1.11 | H | H | $CH_3$ | H | H | F | H | $CH_3$ | $CH_3$ | CH |
| 1.12 | H | H | $CH_3$ | H | H | F | H | $OCH_3$ | $OCH_3$ | CH |
| 1.13 | H | H | $CH_3$ | H | H | F | H | $OCH_3$ | $CH_3$ | CH |
| 1.14 | H | H | $CH_3$ | H | H | F | H | $OCH_3$ | $CH_3$ | N |
| 1.15 | H | H | $CH_3$ | H | H | Cl | H | $OCH_3$ | $CH_3$ | N |
| 1.16 | H | H | $CH_3$ | H | H | Cl | H | $OCH_3$ | $CH_3$ | CH |
| 1.17 | H | H | $CH_3$ | H | H | Cl | H | $OCH_3$ | $OCH_3$ | CH |
| 1.18 | H | H | H | H | $CH_3$ | Cl | H | $OCH_3$ | $OCH_3$ | CH |
| 1.19 | H | H | H | H | $CH_3$ | Cl | H | $OCH_3$ | $CH_3$ | CH |
| 1.20 | H | H | H | H | $CH_3$ | Cl | H | $OCH_3$ | $CH_3$ | N |
| 1.21 | H | H | H | H | $CH_3$ | Cl | H | $CH_3$ | $CH_3$ | CH |
| 1.22 | H | H | H | H | $CH_3$ | F | H | $CH_3$ | $CH_3$ | CH |
| 1.23 | H | H | H | H | $CH_3$ | F | H | $OCH_3$ | $CH_3$ | CH |
| 1.24 | H | H | H | H | $CH_3$ | F | H | $OCH_3$ | $CH_3$ | N |
| 1.25 | H | H | H | F | F | F | H | $OCH_3$ | $CH_3$ | N |
| 1.26 | H | H | H | F | F | F | H | $OCH_3$ | $CH_3$ | CH |
| 1.27 | H | H | H | F | F | F | H | $CH_3$ | $CH_3$ | CH |
| 1.28 | H | H | H | H | F | F | H | $CH_3$ | $CH_3$ | CH |
| 1.29 | H | H | H | H | F | F | H | $OCH_3$ | $CH_3$ | CH |
| 1.30 | H | H | H | H | F | F | H | $OCH_3$ | $CH_3$ | N |
| 1.31 | H | F | F | H | F | Cl | H | $OCH_3$ | $CH_3$ | N |
| 1.32 | H | F | F | H | F | Cl | H | $OCH_3$ | $CH_3$ | CH |
| 1.33 | H | F | F | H | F | Cl | H | $CH_3$ | $CH_3$ | CH |
| 1.34 | H | F | F | H | F | H | H | $CH_3$ | $CH_3$ | CH |
| 1.35 | H | F | F | H | F | H | H | $OCH_3$ | $CH_3$ | CH |
| 1.36 | H | F | F | H | F | H | H | $OCH_3$ | $CH_3$ | N |
| 1.37 | H | F | F | H | F | $CF_3$ | H | $OCH_3$ | $CH_3$ | N |
| 1.38 | H | F | F | H | F | $CF_3$ | H | $OCH_3$ | $CH_3$ | CH |
| 1.39 | H | F | F | H | F | $CF_3$ | H | $CH_3$ | $CH_3$ | CH |
| 1.40 | H | H | H | F | F | F | H | $OCH_3$ | $OCH_3$ | CH |
| 1.41 | H | H | H | H | F | F | H | $OCH_3$ | $OCH_3$ | CH |
| 1.42 | H | F | F | H | F | Cl | H | $OCH_3$ | $OCH_3$ | CH |
| 1.43 | H | F | F | H | F | $CF_3$ | H | $OCH_3$ | $OCH_3$ | CH |
| 1.44 | H | H | H | H | $CH_3$ | F | H | $OCH_3$ | $OCH_3$ | CH |
| 1.45 | H | H | H | H | H | Cl | H | $OCH_3$ | $CH_3$ | CH |
| 1.46 | H | H | H | H | H | Cl | H | $CH_3$ | $CH_3$ | CH |
| 1.47 | H | H | H | H | $C_2H_5$ | F | H | $OCH_3$ | $OCH_3$ | CH |
| 1.48 | H | H | H | H | H | Cl | H | $CH_3$ | $CH_3$ | CH |
| 1.49 | H | H | H | H | H | Cl | H | $OCH_3$ | $CH_3$ | CH |
| 1.50 | H | H | H | F | F | F | H | $OCH_3$ | Cl | CH |
| 1.51 | H | H | H | F | F | F | H | $OCH_2CF_3$ | $N(CH_3)_2$ | N |
| 1.52 | H | H | H | F | F | F | H | $OCH_3$ | $OCH_3$ | CH |
| 1.53 | H | H | $CH_3$ | H | $CH_3$ | Cl | H | $OCH_3$ | $OCH_3$ | CH |
| 1.54 | H | H | H | H | $CH_3$ | Cl | H | $OCH_3$ | $CH_3$ | N |
| 1.55 | H | H | $C_2H_5$ | H | H | Cl | H | $OCH_3$ | $OCH_3$ | CH |
| 1.56 | H | H | $C_2H_5$ | H | H | Cl | H | $OCH_3$ | $CH_3$ | CH |
| 1.57 | H | H | $C_2H_5$ | H | H | Cl | H | $CH_3$ | $CH_3$ | CH |
| 1.58 | H | H | $CH_3$ | H | H | Cl | H | $CH_3$ | $CH_3$ | CH |
| 1.59 | H | H | H | H | $C_2H_5$ | Cl | H | $OCH_3$ | $OCH_3$ | CH |
| 1.60 | H | H | H | H | $C_2H_5$ | Cl | H | $OCH_3$ | $CH_3$ | CH |
| 1.61 | H | H | H | F | F | F | H | $OC_2H_5$ | cyclopropyl | N |
| 1.62 | H | H | H | F | F | F | H | $OCH_3$ | $CH_3$ | N |
| 1.63 | H | H | H | F | F | F | H | $OCH_2CH_3$ | $NHCH_3$ | N |
| 1.64 | H | H | H | F | F | F | H | $CH_3$ | $CH_3$ | CH |
| 1.65 | H | H | H | F | F | F | H | $OCH_3$ | $CH_3$ | CH |
| 1.66 | H | H | H | F | H | Cl | H | $OCH_3$ | $OCH_3$ | CH |
| 1.67 | H | H | H | F | H | $CH_2Cl$ | H | $OCH_3$ | $OCH_3$ | CH |
| 1.68 | H | H | H | F | F | F | H | $OCH_3$ | $NHCH_3$ | CH |

TABLE 1-continued

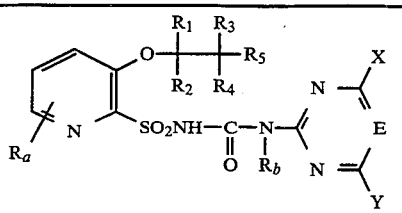

| No. | $R_a$ | $R_1$ | $R_2$ | $R_3$ | $R_4$ | $R_5$ | $R_b$ | X | Y | E |
|---|---|---|---|---|---|---|---|---|---|---|
| 1.69 | H | H | H | Cl | H | $CH_2Cl$ | H | $OCH_3$ | $CH_3$ | CH |
| 1.70 | H | H | H | Cl | H | $CH_2Cl$ | H | $OCH_3$ | $CH_3$ | CH |
| 1.71 | H | H | H | F | F | F | H | $OCH_3$ | ◁ | CH |
| 1.72 | H | H | H | H | H | $CH_2Cl$ | H | $OCH_3$ | $OCH_3$ | CH |
| 1.73 | H | H | $C_2H_5$ | H | H | F | H | $OCH_3$ | $OCH_3$ | CH |
| 1.74 | H | H | $CH_3$ | H | $CH_3$ | F | H | $OCH_3$ | $OCH_3$ | CH |

1.75

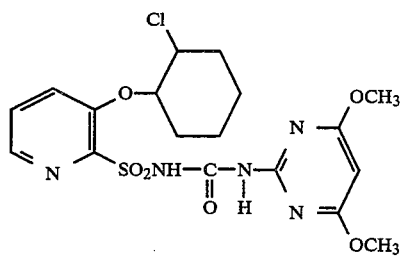

1.76

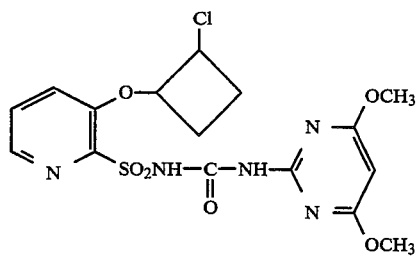

The melting points (m.p.) for the following compounds listed in Table 1 are given in the following:

| Compound No. | M.p. | Compound No. | M.p. |
|---|---|---|---|
| 1.01 | 127–128° C. | 1.24 | 142–144° C. |
| 1.02 | 134–135° C. | 1.44 | 140–142° C. |
| 1.03 | 158–160° C. | 1.45 | 134–136° C. |
| 1.04 | 133–136° C. | 1.46 | 154–156° C. |
| 1.05 | 128–130° C. | 1.47 | 126–128° C. |
| 1.06 | 138–140° C. | 1.51 | 160–162° C. |
| 1.07 | 133–135° C. | 1.52 | 94–96° C. |
| 1.08 | 158–160° C. | 1.53 | 131–133° C. |
| 1.09 | 163–167° C. | 1.54 | 130–132° C. |
| 1.12 | 118–120° C. | 1.55 | 143–145° C. |
| 1.15 | 135–137° C. | 1.58 | 144–147° C. |
| 1.16 | 121–123° C. | 1.59 | 144–146° C. |
| 1.17 | 148–150° C. | 1.60 | 99–101° C. |
| 1.18 | 138–140° C. | 1.61 | 150–152° C. |
| 1.20 | 142–144° C. | 1.62 | 153–155° C. |
| 1.22 | 139–141° C. | 1.64 | 143–145° C. |
| 1.23 | 122–124° C. | 1.65 | 150–152° C. |
| | | 1.66 | 152–155° C. |
| | | 1.67 | 156–158° C. |
| | | 1.68 | 167–170° C. |
| | | 1.69 | 126–128° C. |
| | | 1.70 | 112–115° C. |
| | | 1.71 | 160–163° C. |
| | | 1.72 | 138–140° C. |
| | | 1.73 | 142–144° C. |
| | | 1.74 | 151–153° C. |
| | | 1.75 | 152–155° C. |
| | | 1.76 | 167–169° C. |

TABLE 2

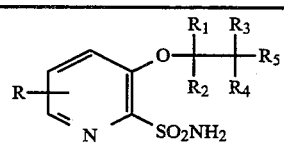

(intermediates)

| No. | $R_a$ | $R_1$ | $R_2$ | $R_3$ | $R_4$ | $R_5$ | M.p. |
|---|---|---|---|---|---|---|---|
| 2.1 | H | H | H | $CH_3$ | Cl | $CH_2Cl$ | |
| 2.2 | H | H | H | H | H | Cl | 136–138° C. |
| 2.3 | H | H | H | H | H | F | 122–123° C. |
| 2.4 | H | H | $CH_3$ | H | H | F | 104–106° C. |
| 2.5 | H | H | $CH_3$ | H | H | Cl | 94–96° C. |
| 2.6 | H | H | $CH_3$ | H | $CH_3$ | Cl | oil |
| 2.7 | H | H | $CH_3$ | H | $CH_3$ | F | |
| 2.8 | H | H | $CH_3$ | F | F | F | |
| 2.9 | H | H | $CH_3$ | F | F | F | |
| 2.10 | H | F | F | H | F | Cl | |
| 2.11 | H | F | F | H | F | H | |
| 2.12 | H | F | F | H | F | $CF_3$ | |
| 2.13 | H | H | H | H | $CH_3$ | Cl | 122–123° C. |
| 2.14 | H | H | H | H | $CH_3$ | F | 116–117° C. |

TABLE 2-continued $$\text{(II)}\quad R{-}\underset{N}{\underset{\|}{\overset{}{\bigcirc}}}\underset{SO_2NH_2}{\overset{O{-}\overset{R_1}{\underset{R_2}{C}}{-}\overset{R_3}{\underset{R_4}{C}}{-}R_5}{}}$$

(intermediates)

| No. | $R_a$ | $R_1$ | $R_2$ | $R_3$ | $R_4$ | $R_5$ | M.p. |
|---|---|---|---|---|---|---|---|
| 2.15 | H | H | H | H | $C_2H_5$ | F | 81–82° C. |
| 2.16 | H | H | H | F | F | F | 136–138° C. |
| 2.17 | H | H | $C_2H_5$ | H | H | Cl | 107–109° C. |
| 2.18 | H | H | H | H | $C_2H_5$ | Cl | 122–124° C. |
| 2.19 | H | H | H | F | H | Cl | 127–130° C. |
| 2.20 | H | H | H | F | H | $CH_2Cl$ | 107–109° C. |
| 2.21 | H | H | H | h | h | $CH_2Cl$ | 136–137° C. |
| 2.22 | H | H | $C_2H_5$ | H | H | F | 77–79° C. |
| 2.23 | H | H | $CH_3$ | H | $CH_3$ | F | |

2.24    150–151° C.

2.25    119–121° C.

BIOLOGICAL EXAMPLES

Example B1: Pre-emergence herbicidal action on plants

Plastics pots are filled with expanded vermiculite (density 0.135 g/cm$^3$, water adsorption capacity 565 g/l). After saturating the non-adsorptive vermiculite with an aqueous emulsion of test compound in deionised water that contains the test compounds in a concentration of 70.8 ppm, seeds of the following plants are sown on the surface: *Nasturtium officinalis, Agrostis tenuis, Stellaria media* and *Digitaria sanguinalis*. The test containers are then kept in a climatic chamber at a temperature of 20° C., an illumination of approximately 20 klux and a relative humidity of 70%. During a germination phase of 4 to 5 days, the pots are covered with transparent material in order to increase the local humidity, and watered with deionised water. After the 5th day, 0.5% of a customary commercial liquid fertilizer is added to the water. 12 days after sowing, the test is evaluated and the action on the test plants is assessed in accordance with the following scale:

1: plants have not germinated or have died.
2–3: very pronounced phytotoxic action
4–6: medium action
7–8: weak action
9: no action, the plants grow like untreated control plants.

The tested compounds of Table 1 exhibit a strong herbicidal action in this test.

Example B2: Post-emergence herbicidal action (contact herbicide)

A number of weeds, both monocotyledonous and dicotyledonous, are sprayed postemergence (at the 4- to 6-leaf stage) with an aqueous active ingredient dispersion at a rate of 8–500 g of test compound per hectare and kept at 24°–26° C. and 45°–60% relative humidity. Three weeks later, the test is evaluated and the herbicidal action is assessed according to a scale of nine ratings (1=complete destruction, 9=no action) in comparison with an untreated control group. Ratings of 6 to 9 (especially 7 to 9) indicate a good tolerance (especially in the case of cultivated plants). The tested compounds of Table 1 exhibit a strong herbicidal action in this test.

Example B3: Herbicidal action in wild rice (paddy)

The weeds *Echinochloa crus-galli* and *Monochoria vag.*, which occur in water, are sown in plastics beakers (surface: 60 cm$^2$; volume: 500 ml). After sowing, the beakers are filled with water up to the surface of the soil. 3 days after sowing, the water level is increased to slightly above the soil surface (3–5 mm). Application is effected 3 days after sowing by spraying the beakers with the test compounds. The rate of application corresponds to a concentration of 8–500 g of active ingredient per hectare. The beakers are then kept in the greenhouse under optimum growth conditions for rice weeds, i.e. at 25°–30° C. and at high humidity. The evaluation of the tests takes place 3 weeks after application. The tested compounds of Table 1 damage the rice weeds during this time.

What is claimed is:

1. An N-pyridinesulfonyl-N'-pyrimidinyl-urea of formula I

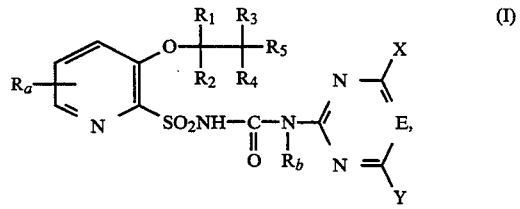

wherein
$R_1$ is hydrogen or fluorine;
or $R_1$ together with $R_3$ is a $C_2$–$C_4$alkylene chain;
$R_3$ is hydrogen, fluorine or $C_1$–$C_3$alkyl;
$R_2$ is hydrogen, fluorine or $C_1$–$C_3$alkyl;
$R_4$ is hydrogen, fluorine, chlorine or $C_1$–$C_3$alkyl;
$R_5$ is hydrogen, fluorine, chlorine, $C_1$–$C_3$alkyl, or $C_1$–$C_3$alkyl substituted by fluorine or chlorine;
$R_a$ is hydrogen or halogen, or a $C_1$–$C_4$alkyl, $C_1$–$C_4$alkoxy or $C_1$–$C_4$alkylthio radical each of which may be unsubstituted or mono- or poly-substituted by halogen;
$R_b$ is hydrogen or a $C_1$–$C_4$alkyl radical;
X is $C_1$–$C_3$alkyl, $C_1$–$C_3$alkyl mono- to tri-substituted by halogen, $C_1$–$C_3$alkoxy, or $C_1$–$C_3$alkoxy mono- to tri-substituted by halogen;
Y is halogen, $C_1$–$C_3$alkyl, $C_1$–$C_3$alkyl mono- to tri-substituted by halogen, $C_1$–$C_3$alkoxy, or $C_1$–$C_3$alkoxy mono- to tri-substituted by halogen, or is cyclopropyl, methylamino or dimethylamino; and
E is the methine group,
or a salt of such a compound, with the proviso that at least one of the radicals $R_1$ to $R_5$ is fluorine, or one of the radicals $R_4$ and $R_5$ is chlorine.

2. A compound of formula I according to claim 1, wherein $R_1$ and $R_3$, each independently of the other, are hydrogen or fluorine; $R_2$ is hydrogen, fluorine or $C_1$–C-

$_3$alkyl; R$_4$ is hydrogen, fluorine or chlorine; and R$_5$ is hydrogen or fluorine, or C$_1$–C$_3$alkyl that is unsubstituted or substituted by fluorine or chlorine.

3. A compound according to claim 1, wherein R$_a$ and R$_b$ are each hydrogen.

4. A compound according to claim 1, wherein the radical of the formula Ia

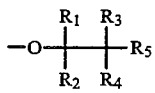

contains a maximum of 3 carbon atoms.

5. A compound according to claim 1, wherein in the radical of the formula Ia

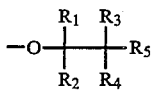

at least one of the radicals R$_3$, R$_4$ and R$_5$ contains a halogen atom indicated for that radical.

6. A compound according to claim 5, wherein only one of the radicals R$_3$, R$_4$ and R$_5$ is halogen.

7. A compound according to claim 1, wherein one of the radicals X and Y is methyl, methoxy, ethoxy, difluoromethoxy or chlorine.

8. A compound according to claim 1, wherein R$_1$ is hydrogen or fluorine; R$_2$ is hydrogen, fluorine, methyl or ethyl; R$_3$ is hydrogen, fluorine or methyl, or R$_1$ together with R$_3$ forms a C$_4$alkylene chain; R$_4$ is hydrogen, fluorine, chlorine, methyl or ethyl; R$_5$ is hydrogen, fluorine, chlorine, trifluoromethyl or dichloromethyl; R$_a$ and R$_b$ are each hydrogen; X is methyl, methoxy, ethoxy, difluoromethoxy or 2,2,2-trifluoroethoxy; and Y is chlorine, methyl, cyclopropyl, methoxy, difluoromethoxy, methylamino or dimethylamino.

9. The compound according to claim 1 N-[3-(2-chloroethoxy)-pyridine-2-sulfonyl]-N'-(4,6-dimethoxypyrimidin-2-yl)urea.

10. A herbicidal and plant-growth-inhibiting composition comprising an active ingredient and a carrier, wherein the active ingredient is a sulfonylurea of formula I according to claim 1.

11. A composition according to claim 10, wherein the sulfonylurea of formula I is from 0.1% to 95% of the composition.

12. A method of controlling undesired plant growth which comprises applying to the plants or to the locus thereof an effective amount of a compound of formula I, according to claim 1, or of a composition comprising that compound.

13. A method according to claim 12, which comprises applying the active ingredient in an amount of from 0.001 to 2 kg per hectare.

14. A method according to claim 12 for the selective pre- or post-emergence control of weeds in crops of useful plants.

15. A method of inhibiting plant growth which comprises applying to the plants or to the locus thereof an effective amount of a compound of formula I, according to claim 1, or of a composition comprising that compound.

* * * * *